US010532078B2

(12) United States Patent
Mandeau et al.

(10) Patent No.: US 10,532,078 B2
(45) Date of Patent: *Jan. 14, 2020

(54) METHOD FOR PRODUCING AN EXTRACT OF A MATRIX OF VEGETABLE ORIGIN BY EXTRUSION WITH A HYDROTROPE SOLUTION

(71) Applicant: PIERRE FABRE DERMO-COSMETIQUE, Boulogne-Billancourt (FR)

(72) Inventors: Anne Mandeau, Toulouse (FR); Mathieu Leti, Montgiscard (FR)

(73) Assignee: PIERRE FABRE DERMO-COSMETIQUE, Boulogne-Billancourt (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/558,427

(22) PCT Filed: Mar. 18, 2016

(86) PCT No.: PCT/EP2016/056039
§ 371 (c)(1),
(2) Date: Sep. 14, 2017

(87) PCT Pub. No.: WO2016/146838
PCT Pub. Date: Sep. 22, 2016

(65) Prior Publication Data
US 2018/0055900 A1 Mar. 1, 2018

(30) Foreign Application Priority Data
Mar. 18, 2015 (FR) ..................................... 15 52249

(51) Int. Cl.
| | |
|---|---|
| *A61K 36/00* | (2006.01) |
| *A61K 36/61* | (2006.01) |
| *A23L 33/105* | (2016.01) |
| *A61K 36/185* | (2006.01) |
| *A61K 36/28* | (2006.01) |
| *A23P 30/20* | (2016.01) |
| *A61K 8/9789* | (2017.01) |
| *A61K 8/02* | (2006.01) |
| *A61K 9/00* | (2006.01) |
| *A61K 9/06* | (2006.01) |
| *A61K 9/48* | (2006.01) |

(52) U.S. Cl.
CPC ............ *A61K 36/61* (2013.01); *A23L 33/105* (2016.08); *A23P 30/20* (2016.08); *A61K 8/0216* (2013.01); *A61K 8/9789* (2017.08); *A61K 9/0014* (2013.01); *A61K 9/0053* (2013.01); *A61K 9/06* (2013.01); *A61K 9/48* (2013.01); *A61K 36/185* (2013.01); *A61K 36/28* (2013.01); *A23V 2002/00* (2013.01); *A61K 2236/00* (2013.01); *A61K 2236/10* (2013.01); *A61K 2236/30* (2013.01); *A61K 2800/48* (2013.01)

(58) Field of Classification Search
None
See application file for complete search history.

(56) References Cited

U.S. PATENT DOCUMENTS

| | | | |
|---|---|---|---|
| 6,224,877 B1 * | 5/2001 | Gaikar ............... | A61K 36/9066 424/756 |
| 6,365,601 B1 | 4/2002 | Gaikar et al. | |
| 2005/0008753 A1 | 1/2005 | Honda et al. | |
| 2008/0138469 A1 | 6/2008 | Nagao et al. | |

FOREIGN PATENT DOCUMENTS

| | | |
|---|---|---|
| CN | 104233892 A * | 12/2014 |
| EP | 1 452 095 A1 | 9/2004 |
| JP | 2009-203229 A | 9/2009 |
| KR | 10-0810533 B1 | 3/2008 |

OTHER PUBLICATIONS

Takayanagi et al, Sesquiterpene lactone glucosides and alkyl glycosides from the fruit of cumin. Phytochemistry (2003), vol. 63, No. 4, pp. 479-484 (Year: 2003).*
Coffman et al., "Self-Association of Nicotinamide in Aqueous Solution: Light-Scattering and Vapor Pressure Osmometry Studies," J. Pharmaceutical Sciences, vol. 85, No. 8, Aug. 1996 (Abstract published Jun. 15, 1996), pp. 848-853.
Da Silva et al., "Investigations on the Mechanism of Aqueous Solubility Increase Caused by Some Hydrotropes," Thermochimica Acta, vol. 328, 1999, pp. 161-167.
Dandekar et al., "Hydrotropic Extraction of Bioactive Limonin from Sour Orange (Citrus aurantium L.) Seeds," Food Chemistry, vol. 109, 2008, pp. 515-520.
Dziezak (Editor), "Single- and Twin-Screw Extruders in Food Processing," Food Technology, Apr. 1989, pp. 164-174.
French Search Report for French Application No. 1552249, dated Jul. 20, 2015.
Marechal et al., "Characterization of By-Products of Sunflower Culture—Commericial Applications for Stalks and Heads," Industrial Crops and Products, vol. 10, 1999, pp. 185-200.
N'Diaye et al., "Extraction of Hemicelluloses from Poplar, *Populus tremuloides*, Using an Extruder-Type Twin-Screw Reactor: A Feasibility Study," Bioresource Technology, vol. 57, 1996, pp. 61-67.
Sriti et al., "Oil Extraction from Coriander Fruits by Extrusion and Comparison with Solvent Extraction Processes," Industrial Crops and Products, vol. 33, 2011 (published on web Jan. 26, 2011), pp. 659-664.
White et al., "Polyphenolic Composition and Antioxidant Capacity of Extruded Cranberry Pomace," J. Agric. Food. Chem., vol. 58, No. 7, 2010 (published on web Dec. 18, 2009), pp. 4037-4042.
International Search Report, issued in PCT/EP2016/056039 (PCT/ISA/210), dated May 25, 2016.
Written Opinion of the International Searching Authority, issued in PCT/EP2016/056039 (PCT/ISA/237), dated May 25, 2016.

* cited by examiner

*Primary Examiner* — Qiuwen Mi
(74) *Attorney, Agent, or Firm* — Birch, Stewart, Kolasch & Birch, LLP

(57) ABSTRACT

The invention relates to a method for producing an extract of a matrix of vegetable origin, particularly a plant, characterised in that the matrix of vegetable origin undergoes a mechanical treatment consisting in extruding the matrix of vegetable origin in an extruder, in association or not with a heat treatment, in the presence of an aqueous solution containing at least one hydrotrope agent, particularly at a concentration at least equal to the minimum hydrotrope concentration thereof, followed by an operation of recovering the extract.

16 Claims, 1 Drawing Sheet

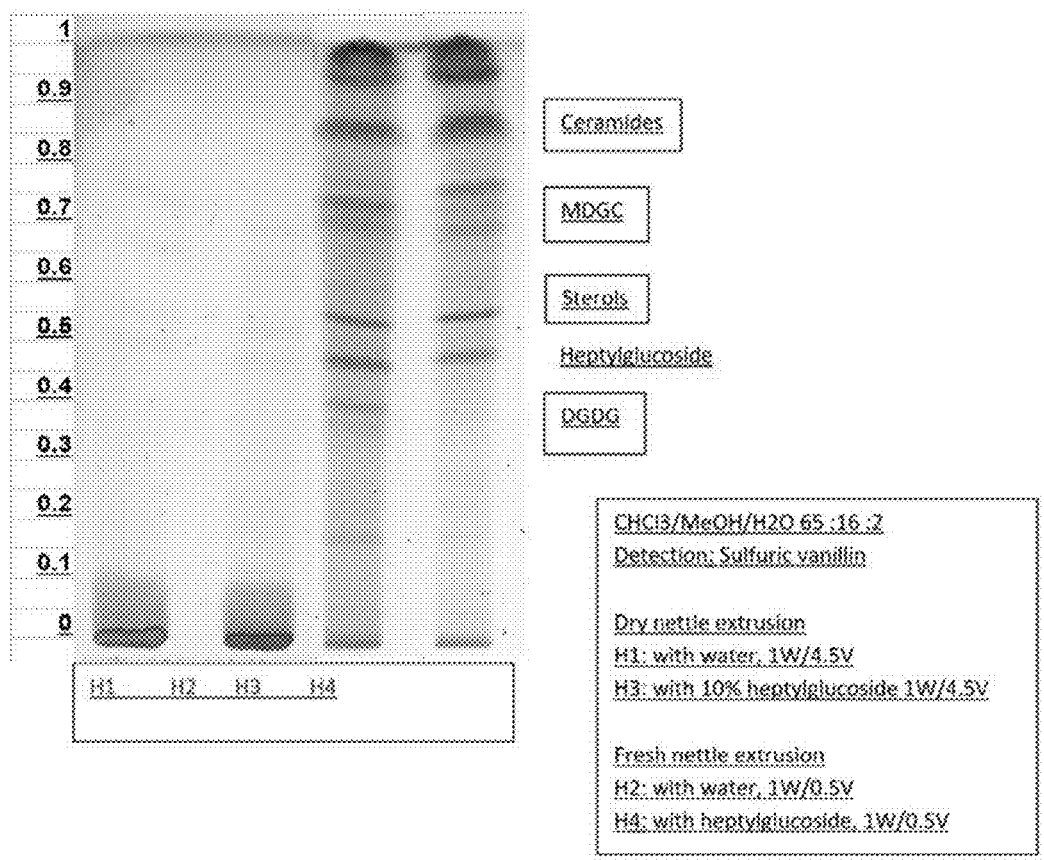

METHOD FOR PRODUCING AN EXTRACT OF A MATRIX OF VEGETABLE ORIGIN BY EXTRUSION WITH A HYDROTROPE SOLUTION

The field of the present invention pertains to a method for producing a vegetable matrix extract by extrusion with a hydrotropic solution.

Extrusion is a process whereby a material able to flow under various controlled conditions is forced to pass through a die at a determined rate (Dziezak, J. D. (1989). Single and twin-screw extruders in food processing. Food Technol., April, 164-174). Initially, this technology was used in the metallurgical industry in England at the end of the 18th century. Later on, it was introduced into the agri-food industry for the production of sausage and pasta products. The food industry currently makes abundant use of this extrusion technique for baking-extrusion of starchy products (biscuits, rusks, snacks, etc.) but also for texturizing proteins and for the production of pet food and animal feed products.

In parallel, extrusion technology was largely developed for the thermoplastics industry and led to the design of new screws, further progress in the technology and the extension towards new applications.

Several studies have focused on the use of an extruder to conduct chemical, mechanical, thermomechanical actions in a single step and continuously, e.g. for the extraction of hemicelluloses (N'Diaye, S., Rigal, L., Larocque, P., Vidal, P. F., 1996. Extraction of hemicelluloses from poplar populus tremuloides, using an extruder type twin-screw reactor: A feasibility study. Bioresearch Technology 57, 61-67), of pectins (Marechal V., Rigal L. Characterization of by-products of sunflower culture—Commercial applications for stalks and heads (1999) Industrial Crops and Products, 10 (3), pp. 185-200). etc. In these cases, an acid or basic solvent is added to the extruder at the same time as the raw vegetable material, to facilitate extraction and solubilisation of the desired macromolecules (reactive extrusion).

Some applications are already known for vegetable extraction: the use of a single-screw extruder to express oils from oil seeds without any injection of solvent into the barrel, this oil extraction being based on compression of the solid (Sriti J., Talou T., Faye M., Vilarem G. and Marzouk B. Oil extraction from coriander fruits by extrusion and comparison with solvent extraction processes. (2011) Industrial Crops and Products, 33, 659-664).

Extrusion is also used for the pre-treatment of fruit pomace (apple, blackcurrant, cranberry) in association with a solid medium such as corn starch, to increase the extraction of phenolic compounds (White Brittany L., Howard Luke L., Prior Ronald L, Polyphenolic composition and antioxidant capacity of extruded cranberry pomace. (2010), J. Agric. Food Chem. 58, 4037-4042.).

In the sphere of vegetable extraction, as a function of the solvent used, the membranes of the vegetable cells are more or less weakened, which may or may not allow release of the compounds they contain.

Water is certainly a natural solvent considered to be renewable; however, its strong polarity does not allow the extraction of some lipophilic molecules of interest.

Hydrotropic agents are water-soluble organic compounds which, on and after a certain concentration known as "MHC" (Minimum Hydrotropic Concentration), allow a significant increase in the solubility of organic compounds that are practically insoluble in water under normal conditions. Hydrotropes are amphilphilic and may be ionic (anionic, cationic, zwitterionic) or non-ionic (resorcinol, nicotinamide, alkyl polyglycosides etc.) and may have various structures e.g. aromatic, aliphatic, cyclic or not. Hydrotropic agents are compounds soluble in water in any proportion and not having any surfactant property.

The minimum hydrotropic concentration (MHC) is the concentration on and after which hydrotropes start to form aggregates i.e. new micro-environments with physical properties differing from those observed when the compound is diluted, and differing from micellar behaviour. This minimum hydrotropic concentration is specific to each hydrotrope and is generally of the order of magnitude of molarity. It can be determined with several physicochemical methods such as measurement of surface tension, conductivity, or dynamic or static light scattering (Self-association of Nicotinamide in aqueous solution: Light-scattering and vapor pressure osmometry studies (1996) 85(8): 848-853).

MHC can be determined using several physicochemical methods such as measurement of surface tension, conductivity, dynamic and static light scattering (Self-association of Nicotinamide in aqueous solution: Light-scattering and vapor pressure osmometry studies (1996) 85(8): 848-853) or quite simply by plotting a solubilisation curve of a lipophilic compound (content of solubilised solute vs. hydrotrope concentration). Sudan Red, a lipophilic dye easily assayed by spectrophotometry, can be used as reference. The value of this concentration is dependent on type of hydrotrope and not type of solute. It corresponds to the minimum concentration on and after which the solubilisation curve of the solute becomes exponential.

The potential of hydrotropes as solubilisation adjuvants in an aqueous medium for some molecules has been investigated. (Da Silva R. C., Spitzer M., Da Silva L. H. M., Loh W. Investigations on the mechanism of aqueous solubility increase caused by some hydrotropes. (1999) Thermochimica Acta 328, 161-167). The potential of ionic hydrotropes as adjuvants for the extraction of metabolites of plant origin in an aqueous medium has also been demonstrated (Dandekar D. V., Jayaprakasha G. K., Patil B. S., Hydrotropic extraction of bioactive limonin from sour orange (*Citrus aurantium* L.) seeds. (2008) Food Chemistry, 109, 515-520).

There is still a need to improve existing extraction methods for the purpose inter alia of reducing the environmental impact thereof and improving the quality of the extract obtained.

The Applicant has evidenced that a method to produce an extract of a vegetable matrix by extrusion with a hydrotropic solution is particularly advantageous, since it allows extracts to be obtained that are rich in compounds of interest and over wider polarity ranges; whilst reducing energy consumption. Advantageously, the method also offers the possibility of using alternative solvents to conventional solvents derived from the petrochemical industry, and that are both eco-friendly and lead to obtaining extracts that are particularly adapted for pharmaceutical, cosmetic or agri-food use.

BRIEF DESCRIPTION OF THE DRAWING

FIG. 1 is a thin layer chromatography analysis of an extract of dry nettle and an extract of fresh nettle.

The present invention concerns a method to extract dry or fresh vegetable matrixes by extrusion in the presence of an aqueous hydrotropic solution containing at least one hydrotropic agent of ionic or non-ionic type, in sufficient amount for the extraction of lipophilic compounds. The extrusion allows a total extract to be obtained in very short time, with a much lower weight/solvent ratio than in conventional extraction and with comparable, even better quality. The environmental impact of the method is therefore largely improved. In addition, in the present invention, the extract may be either total (containing polar, moderately polar and lipophilic compounds) or enriched with lipophilic compounds of interest due to the selectivity of extraction with the hydrotropic solution.

More specifically, the invention concerns a method to obtain a vegetable matrix extract, characterized in that said fresh or dry vegetable matrices are subjected to mechanical treatment whereby the matrix is extruded in an extruder, associated or not with heat treatment, in the presence of an aqueous solution containing at least one hydrotropic agent preferably at minimum hydrotropic concentration, followed by an operation to recover the extract.

By aqueous solution containing at least one hydrotropic agent at a concentration at least equal to the minimum hydrotropic concentration (MHC), according to the invention, is meant an aqueous solution containing at least one hydrotropic agent at a concentration equal to or higher than the previously indicated minimum hydrotropic concentration (MHC). Consideration must also be given to the content of water which may be contained in the vegetable matrix, and the concentration of hydrotropic agents adjusted accordingly to allow proper use thereof in the method of the present invention.

According to another characteristic of the invention, the concentration of hydrotropic agent in said aqueous solution is between 1 and 10 times, preferably 1 and 6 times, more preferably between 1 and 2 times, further preferably between 1.4 and 1.8 times the minimum hydrotropic concentration (MHC). Advantageously, in practice the hydrotropic agent can be used in an aqueous solution at a concentration of 1.5 mol/L.

According to another advantageous characteristic of the present invention, the hydrotropic agent is contained in the aqueous extraction solution at a concentration lower than 60% by weight relative to the weight of said solution, preferably lower than 50% by weight relative to the weight of said solution, more preferably lower than 40% by weight relative to the weight of said solution, further preferably lower than 30% by weight relative to the weight of said solution. It will particularly be observed that this concentration threshold implicitly dispenses with the use of ethanol as solvent to extract lipophilic compounds, insofar as ethanol is generally used in much higher contents, of the order of 80%. In addition, the use of ethanol ins an extruder necessarily implies a secure environment on account of the risks incurred through the volatility and flammability of this particular solvent.

In one particular embodiment of the invention, the ionic or non-ionic hydrotrope can be selected from the group composed of: sodium n-butyl benzene sulfonate, sodium cumene sulfonate, sodium paratoluene sulfonate or sodium xylene sulfonate, heptyglucoside alkylglycosides and alkylpolyglycosides, dimethyl isosorbide, N,N-diethylnicotinamide, N,N-dimethylbenzamide, isopentyldiol, used alone or in a mixture.

By "lipophilic compounds", in the present invention, is meant compounds with a positive octanol-water partition coefficient, also known as log P or log kow.

According to one characteristic of the invention, the hydrotropic agent is of ionic type, selected in particular from among alkylbenzene sulfonates such as sodium cumene sulfonate and sodium xylene sulfonate.

According to one advantageous characteristic of the invention, the hydrotropic agent is of non-ionic type, preferably agri-sourced, selected in particular from among alkyl(poly)glycosides of general formula Alk-O-Zp where:

Alk designates a hydrophobic, aliphatic hydrocarbon fragment, saturated or unsaturated, straight-chain or branched, having 3 to 7 carbon atoms; and Z is a hydrophilic glycoside group such as glucose, xylose and arabinose; and $1<p<5$.

According to one particular embodiment, Z is a glucose group.

According to another particular embodiment of the invention, Z is a xylose group.

According to another particular embodiment of the invention, Z is an arabinose group.

According to one particular embodiment of the invention, Alk designates a hydrophobic, aliphatic hydrocarbon fragment, saturated or unsaturated, straight-chain or branched, having 7 carbon atoms.

According to another particular embodiment of the invention, Alk designates a hydrophobic, aliphatic hydrocarbon fragment, saturated or unsaturated, straight-chain or branched, having 6 carbon atoms.

According to a further particular embodiment of the invention, Alk designates a hydrophobic, aliphatic hydrocarbon fragment, saturated or unsaturated, straight-chain or branched, having 5 carbon atoms.

According to a further particular embodiment of the invention, Alk designates a hydrophobic, aliphatic hydrocarbon fragment, saturated or unsaturated, straight-chain or branched, having 4 carbon atoms.

In another embodiment of the invention, the hydrotropic agent is agri-sourced (of non-petrochemical origin).

According to another characteristic of the invention, the agri-sourced hydrotropic agent is a combination of a C7 fatty alcohol derived from ricin with wheat glucose (GM-free).

According to one advantageous characteristic of the invention, said hydrotropic agent is an amyl-glycoside, the hydrophobic amyl fragment of which corresponds to a C5 alcohol obtained by fermenting beetroot or potato starch, the glycoside fragment being derived from cereals.

According to one advantageous characteristic of the invention, said hydrotropic agent is a combination of a C4 fatty alcohol with a xyloside.

In another particular embodiment of the invention, said preferably agri-sourced hydrotropic agent is a diol, in particular isopentyldiol (3-Methyl-1,3-butanediol).

According to one characteristic of the invention, the hydrotropic agent is of non-ionic type, selected in particular from among isopentyldiol, heptylglucoside and butylxyloside.

The non-ionic, amphiphilic compound, useful in the invention, may advantageously be one of the commercial raw materials SEPICLEAR G7® (SEPPIC), APPY-CLEAN® (WHEATOLEO), Isopentyldiol by Kuraray.

According to another characteristic of the invention, the vegetable matrix undergoes pre-treatment before extrusion. By "pre-treatment", according to the present invention, is meant a treatment selected from among the following treatments: ultrasound, microwave, enzymatic digestion, maceration in the hydrotropic solution, preparation of the vegetable matrix such as cryogenic grinding, fragmentation, grinding etc.

In one particular embodiment of the invention, pre-treatment consists of maceration in the hydrotropic solution before the extrusion step.

By "extrusion" according to the present invention is meant mechanical treatment whereby the vegetable matrix is extruded in a single-screw or twin-screw extruder, with co- or counter-rotating screws, preferably a twin-screw extruder whether or not associated with heat treatment.

Extrusion is conducted at temperatures between 20 and 200° C., preferably between 60 and 120° C.

According to another characteristic of the invention, extrusion is performed in a twin-screw extruder.

According to one advantageous characteristic of the invention, the twin-screw extruder comprises a first co-rotating and co-penetrating twin-screw zone where trituration of said vegetable matrixes takes place.

The method uses an extruder and preferably a twin-screw extruder with several barrels ending in a filtering barrel, allowing variation in temperature and at the same application of shear, intense mixing of the vegetable raw material leading to the entrainment of a large number of compounds, and the break-up of matter.

The extruder is fed with the vegetable matrix and hydrotropic solution at flow rates determined so as to obtain ratios of weight of vegetable matrix (kilo)/volume of solvent (L) ranging from 1W/1V to 1W/10V, preferably 1W/2V to 1W/6V.

The present invention also concerns the use of an aqueous solution containing at least one hydrotropic agent at minimum hydrotropic concentration in a method to extract fresh or dry vegetable matrixes, implemented by mechanical treatment conducted in an extruder. The conditions of extrusion and type of vegetable matrixes used are identical to those described in connection with the method of the invention.

By "vegetable matrix" in the present invention is meant all or part of a plant, fungus, lichen, alga, culture of micro-algae or culture of dedifferentiated vegetable cells.

Said plant, fungus, lichen, alga, are dry or fresh, frozen or unfrozen, and whole (non-fragmented and non-ground), fragmented or ground. Said cultures of micro-algae or of de-differentiated vegetable cells are whole, ground, preferably fresh or dried, filtered to recover the biomass, may or may not have been subjected to pre-treatment to release the intra-cellular content e.g. via ultrasound process.

By "part of plant" is notably meant the above-ground parts such as stems, branches, leaves, fruit, seeds and/or flowers; and/or the below-ground parts such as rhizomes, roots and/or bulbs.

By "part of lichen, fungus or alga" is meant any organ of these organisms such as thalli, sporophores, macromycetes, mycelia and/or filaments.

In one particular embodiment of the invention, use is made of all or part of whole plants (non-fragmented, non-ground).

Among the plants that can be used in the present invention, mention can be made inter alia of: the fruit of *Physalis peruviana*, fruit of *Embelia ribes*, leaves of *Myrtus communis*, leaves of *Eucalyptus globulus*, pericarps of *Garcinia mangostana*, female inflorescences of *Humulus lupulus*, bark of *Cinchona* sp., above-ground parts of *Urtica dioica*, above-ground parts of *Helichrysum* spp., fruit of *Vanilla* spp., rhizomes of *Zingiber officinale*, rhizomes of *Curcuma* spp., rhizomes of *Piper methysticum*, leaves of *Piper* spp., fruit and leaves of *Olea europaea* . . .

Among the algae that can be used in the present invention are particularly meant blue algae or Cyanobacteria, and eukaryotes among which Euglenophytes, Cryptophytes, Haptophytes, Glaucophytes; red algae or Rhodophyta, Stramenopiles in particular grouping together Diatoms and brown algae or Phaeophyceae, and finally green algae which inter alia include Ulvophyceae.

Among the lichens that can be used in the invention, mention can be made inter alia of: the thalli of *Cetraria islandica*, thalli of *Usnea* spp., thalli of *Cladonia* spp., thalli of *Lobaria* spp.

Among the fungi that can be used in the present invention, mention can be made inter alia of: *Coriolus versicolor, Cordyceps* spp.

Among the cultures of vegetable cells that can be used in the present invention, mention can be made inter alia of: cell cultures of *Mimosa pudica, Tripterygium wilfordii*.

In one embodiment, extrusion is characterized by passing the dry or fresh vegetable matrix through a twin-screw extruder composed of:

a feed zone: feed hopper;

the main body of the extruder composed of one or more barrels, containing rotating endless screws (co-rotating or counter-rotating), or screw segments. Preferably, there are several successive adjacent barrels. Preferably, there are two co-rotating endless screws. The profile of the screws may vary depending on the thread of the screws (e.g. trapezoidal, conjugate, single or double . . . ) and on screw pitch. Each of these screws may also have different segments that may differ from one another through the shape of the screw thread and/or pitch. Optionally, some constituent segments of these screws may also correspond to one-lobed or three-lobed mixing elements;

means to feed an aqueous solution of hydrotropic agent acting as solvent, said feed means being coupled to at least one of the barrels;

at least one filtering barrel which:
optionally comes into operation for solid/liquid separation;
also comprises filtering means such as a grid, and;
is particularly positioned at the outlet of the extruder;

heating and cooling means since the barrel must be temperature-regulated: from 20° C. to 200° C.

extruder drive means such as:
a drive unit: composed of a gear motor and torque divider, which provide the mechanical power needed for rotation of the screws;
automated piloting means: for monitoring and controlling the process. The parameters able to be adjusted are: rotation speed of the screws and temperature of each barrel.

The mechanical process of twin-screw extrusion leads to the formation of a vegetable plug which applies pressure on the material causing bursting of cells, breakdown of the vegetable material allowing extraction of a maximum number of compounds that are entrained and solubilised in the hydrotropic solution.

Collection of the extract whereby the solvent containing the compounds of interest is separated from the residual solid residues of the vegetable matrix, can be obtained by clarification and/or filtration.

By "clarification" is meant the removal of cell fragments contained in the extract on leaving the extruder. This removal can be obtained using clarification technology under centrifugal effect, the purpose of which is to removal the solid residue which could clog the filtering media. This removal can also be obtained directly by filtering with an adjuvant.

By "filtration" is meant frontal or tangential filtration for which the presence of a filtering adjuvant can be envisaged (of perlite, diatomaceous type, etc.). This filtering retains the final solid residues, the purpose being to obtain a perfectly clear solution. It can be followed by membrane filtration with a cut-off threshold determined as a function of the size of molecules under consideration. It can also be replaced or followed by filtration on resin or silica to obtain a richer content of compound of interest (e.g. adsorption resins).

In one particular embodiment, the clarification-filtration step is performed using a filtering barrel integrated at the end of the extruder.

In one particular embodiment, the extract is stored as such or freeze-dried comprising the molecules of interest and hydrotrope(s), the latter allowing better solubilisation in the end product.

A total extract is thus obtained containing compounds of wide-ranging polarity (polar, moderately polar, apolar).

The extract can also be diluted in a volume of water to which there may or may not be added one or more adjuvants selected from among salts, acids or bases, to arrive at a final concentration of hydrotropic agent lower than the MHC. It is therefore possible to recover the lipophilic compounds by precipitation and solid/liquid separation, such as filtration or centrifugation.

In this manner, an extract enriched with lipophilic compounds is obtained.

The lipophilic compounds of interest may be flavonoids, phenolic acids, terpene compounds (mono-, di-, triterpenes) and steroid compounds, diarylheptanoid derivatives, lignans, coumarins, quinones, anthraquinones, xanthones, phloroglucinols, iridoids, sesquiterpene lactones, alkaloids, sucroesters, polar lipids . . .

In particular, they may be kavalactones, myrtucommulones, embeline, quinine and derivatives, vanillin and derivatives, α-mangostin, xanthohumol, mono- and di-galactosyldiacylglycerols, maslinic acid, ursolic acid, rosmarinic acid, carnosol, galangin, pinobanksin, cardamonin, curcuminoids, gingerol, shogaol, . . .

The total extract or extract enriched with lipophilic compounds can be diluted, concentrated, dried or stored as such with the addition of a suitable preserving agent that is authorised in the desired end product (such as glycols, or sorbic acid, benzoic acid, citric acid and the salts thereof, etc.) or alcohol (minimum 15°).

For the providing of a dry extract, vacuum drying, lyophilisation or spray-drying technologies can be envisaged. The extract obtained can be dried with or without a medium and/or solubilised in a liquid medium.

The liquid, paste or dry extracts obtained such as defined above can be used as such in cosmetic, pharmaceutical or food compositions, intended to be administered via topical route or oral route.

The advantages of hydrotropic extraction by extrusion in comparison with reactor extraction are:
  significant reduction in the amount of solvent used (on average 2 to 5 times lower);
  significant reduction in extraction time (2 to 5 minutes compared with at least 1 hour)
  possible use of an alternative, agri-sourced solvent (such as polyalkyl glycosides in particular) instead of polluting solvents of petrochemical origin (ethyl acetate, acetone, hexane . . . )
  quality of the extract obtained (extract having wide-ranging polarity or extract enriched with lipophilic compounds of interest; and selectivity also observed among the lipophilic compounds of interest)

According to one preferred embodiment, apart from the hydrotropic solution, no other solvent is used at the extrusion step properly so-called. The hydrotropic solution is the sole solvent involved in the extraction method by extrusion.

The following examples are given as nonlimiting indications.

EXAMPLES

Example 1: Myrtle Extract 1.3 kg of dry leaves of *Myrtus communis* were fed into the first barrel of a Clextral BC45 twin-screw extruder at a rate of 8 kg/H. An aqueous solution of amyl xylosides was then added at 1.5 mol/L and at a rate of 24 L/H. The temperature applied to the different barrels was 60° C./60° C./60° C./60° C./60° C. After 5 minutes, the extract of Myrtle leaves was recovered at the outlet by means of a filtering barrel allowing solid/liquid separation. After clarification, the dry Myrtle extract was obtained with a yield of 81% relative to the solvent used and 1184% relative to the plant feed. The solution was diluted in 4 volumes of water. After centrifugation, the residue corresponding to the extract enriched with Myrtle was obtained with a weight yield of 1.2% relative to plant feed.

For comparison, 1.3 kg of dry leaves of *Myrtus communis* were extracted in water under the same conditions. After clarification, the Myrtle extract was obtained with a yield of 8.5% relative to plant feed.

The myrtucommulones B', S and A were assayed in both extracts and in two extracts obtained in a reactor.

| Extract | Extraction time | Yield | Content of myrtu-commulones in extract (m/m) | Ratio [Myrt. B']/[Myrt. A] |
|---|---|---|---|---|
| Amyl xyloside 1 W/3 V extrusion + precipitation by dilution | 5' | 1.2% | 9.9% | 2.3 |
| Amyl xyloside 1 W/7 V reactor + precipitation by dilution | 3 H | 2.1% | 8.9% | 1.9 |
| Isopropyl acetate 1 W/8 V reactor | 2 H | 3.1% | 7.3% | 3.1 |
| Water 1 W/3 V extrusion | 5' | 8.5% | 0% | / |

Although the extraction weight yield is lower, the extract obtained by extrusion with a plant weight/solvent volume ratio that is non-feasible in a reactor (insufficient for plant wetting) and with an extremely rapid extraction time, has a slightly higher concentration of myrtucommulones than obtained with conventional extraction in a reactor with the same solvent. It also has a higher concentration of myrtucommulones than the extract obtained with isopropyl acetate in a reactor. Myrtucommulone A, the most apolar, is twice richer in the hydrotropic extract obtained by extrusion than in the extract with isopropyl acetate, which evidences the selectivity of the method. The extract obtained by extrusion with water without amyl xylosides does not allow the extraction of compounds of interest.

Example 2: Extract of *Helichrysum gymnocephalum* by Extrusion 5 kg of the entire, dried above-ground parts of *Helichrysum gypmnocephalum* were fed into the first barrel of a Clextral BC45 twin-screw extruder, at a rate of 10 kg/H. An aqueous solution containing 50% heptylglucoside m/m (1.5M) was added at a rate of 60 L/H. The temperature applied to the different barrels was 60° C./60° C./60° C./60° C./60° C. After 5 minutes, the *Helichrysum* extract was recovered at the outlet of the extruder by means of a filtering barrel allowing solid/liquid separation. After clarification, the *Helichrysum* extract was obtained with a yield of 69.5% relative to the solvent used and 407% relative to plant feed.

| Extract | Extraction time | Yield | Content of apolar flavonoids in the non-concentrated, non-dried extract (m/m) |
|---|---|---|---|
| Heptylglucoside 1 W/6 V extrusion | 5' | 407.1% | 0.13% |
| Heptylglucoside 1 W/3 V extrusion | 5' | 196.1% | 0.15% |
| Heptylglucoside 1 W/15 V reactor | 2 H | 1450% | 0.10% |
| Water 1 W/6 V extrusion | 5' | 573% | 0% |

Although the yields are lower, the quality of the extract obtained by extrusion with volumes of solvent up to 5 times lower—a weight/solvent ratio non-feasible in a reactor (insufficient for plant wetting)—and with an extremely rapid extraction time, is comparable with that obtained by conventional extraction with the same solvent. The extract obtained by extrusion with water without heptylglucoside does not allow extraction of these compounds of interest.

Example 3: Extract of Dry Nettle and Fresh Nettle 0.67 kg of the above-ground parts of nettles were fed into the 1$^{st}$ barrel of a Clextral BC45 twin-screw extruder at a rate of 8 kg/H. An aqueous solution containing 10% heptylglucoside m/m was added at a rate of 36 kg/H, which corresponds to extraction with a weight/volume ratio of 1/4.5, non-feasible in batch operation having regard to the low density of the above-ground parts of dry nettles. The temperature applied to the different barrels was 60° C./60° C./60° C./60° C./60° C. After 5 minutes, the dry nettle extract was recovered at the outlet of the extruder by means of a filtering barrel allowing solid/liquid separation. After clarification, the nettle extract was obtained with a yield of 48.7% relative to the solvent used and 218% relative to plant feed.

4.4 kg of fresh nettle, above-ground parts were fed into the 1st barrel of a Clextral BC45 twin-screw extruder at a rate of 33 kg/H. An aqueous solution containing 10% heptylglucoside m/m was added at a rate of 17 kg/H, which corresponds to extraction with a weight/volume ratio of 1/0.5, but in fact 1/6 if consideration is given to the water content of the plant. This is impossible to carry out in batch operation. The temperature applied to the different barrels was 60° C./60° C./60° C./60° C./60° C. After 8 minutes, the fresh nettle extract was recovered at the outlet of the extruder by means of a filtering barrel allowing solid/liquid separation. After clarification, the nettle extract was obtained with a yield of 162.6% relative to the solvent used and 85% relative to plant feed.

The 2 extracts obtained were then acidified with sulfuric acid qs pH3 and diluted 6 times in water to obtain a final heptylglucoside concentration of 1.4%. Turbidity occurred and a residue was collected after centrifugation for 20' at 3500 rpm.

Thin layer chromatography analysis in appended FIG. 1 shows the presence in these 2 extracts of polar lipids such as galactolipids and sterols, these bands not being present for the extract obtained by extrusion using only water under the same conditions (extrusion dry/fresh plant, plant and solvent feed rates). MGDG designates mono-galactosyldiacylglycerol and DGDG designates di-galactosyldiactylglycerol.

Example 4: Capsule

| | |
|---|---|
| Myrtle extract as in Example 1: | 200 mg |
| Starch: | 45 mg |
| Magnesium stearate: | 2 mg |

Example 5: Cream

| | |
|---|---|
| *Helichrysum gymnocephalum* extract as in Ex. 2: | 0.5-3% |
| Tribehenin PEG- 20 esters | 2-7% |
| Isodecyl neopentanoate | 2-9% |
| Glycerine | 0.5-10% |
| Glycol palmitate | 1-6% |
| Cetyl alcohol | 0.5-3% |
| Disodium EDTA | 0.05-0.25% |
| Preserving agents | 0.5-3% |
| Fragrance | 0.2-0.5% |
| Xanthan gum | 0.1-0.4% |
| Water | qs |

The invention claimed is:

1. A method for obtaining an extract of a vegetable matrix, wherein the vegetable matrix is a plant matrix, characterized in that the vegetable matrix is subjected to mechanical treatment consisting of extruding the vegetable matrix in an extruder, associated or not with heat treatment, in the presence of an aqueous solution containing at least one hydrotropic agent, followed by an operation to recover the extract,
   wherein the hydrotropic agent is an alkyl-(poly)glycoside of general formula Alk-O-Zp, where:
      Alk designates a hydrophobic, aliphatic hydrocarbon fragment, saturated or unsaturated, straight-chain or branched, having 3 to 7 carbon atoms, and
      Z is a hydrophilic glycoside group selected from the group consisting of glucose, xylose and arabinose, and 1<p<5.

2. The method according to claim 1, characterized in that said heat treatment is conducted at temperatures between 20° C. and 200° C.

3. The method according to claim 1, characterized in that the plants subjected to thermomechanical treatment in the presence of an aqueous solution of a hydrotropic agent, are composed in full or in part of the above-ground parts and/or below-ground parts of dry plants or fresh plants that are whole, fragmented or ground.

4. The method according to claim 3, characterized in that the plant parts are represented by the above-ground parts, wherein the above-ground part are the stems, branches, leaves, fruit, seeds and/or flowers; and/or the below-ground parts, wherein the below-ground parts are rhizomes, roots and/or bulbs.

5. The method according to claim 1, characterized in that the plants subjected to mechanical treatment in the presence of an aqueous solution of a hydrotropic agent, are selected from among the fruit of *Physalis peruviana*, seeds of *Embe-* lia ribes, leaves of *Myrtus communis*, leaves of *Eucalyptus globulus*, pericarps of *Garcinia mangostana*, female inflorescences of *Humulus lupulus*, bark of *Cinchona* sp., above-ground parts of *Urtica dioica*, above-ground parts of *Helichrysum* spp., fruit of *Vanilla* spp., rhizomes of *Zingiber officinale*, rhizomes of *Curcuma* spp., rhizomes of *Piper methysticum*, leaves of *Piper* spp, fruits and leaves of *Olea europaea*.

6. The method according to claim 1, characterized in that the plants undergo pre-treatment before extrusion, said pre-treatment includes ultrasound, microwave, enzymatic digestion, and/or maceration in the hydrotropic solution, wherein the plant is prepared by cryogenic grinding, fragmentation, or grinding.

7. The method according to claim 1, characterized in that the recovered extract is subjected to a subsequent step of clarification and/or filtration.

8. The method according to claim 1, characterized in that the recovered extract is diluted, concentrated, dried or stored as such with the addition of a suitable preserving agent.

9. The method according to claim 1, characterized in that the recovered extract is diluted in a sufficient volume of water to recover a dry extract enriched with lipophilic compounds.

10. The method according to claim 1, characterized in that extrusion is implemented in a twin-screw extruder.

11. The method according to claim 10, characterized in that the twin-screw extruder comprises a first zone with co-rotating and co-penetrating twin screws, where trituration of said plants takes place.

12. The method according to claim 10, characterized in that the twin-screw extruder comprises a second twin-screw zone where solid/liquid separation takes place.

13. The method according to claim 1, characterized in that said extruder comprises at least one barrel.

14. The method according to claim 1, characterized in that said extruder comprises several successive adjacent barrels.

15. The method according to claim 1, characterized in that said heat treatment is conducted at temperatures between 60° C. and 120° C.

16. The method according to claim 1, wherein the aqueous solution containing at least one hydrotropic agent is at a concentration at least equal to the minimum hydrotropic concentration.

* * * * *